United States Patent [19]
Nur-E-Kamal et al.

[11] Patent Number: 5,580,955
[45] Date of Patent: Dec. 3, 1996

[54] FRAGMENTS OF NEUROFIBROMIN (NF1) AND METHOD TO REVERSE ACTIVATED RAS INDUCED MALIGNANT TRANSFORMATION IN MAMMALIAN CELLS

[75] Inventors: M. S. A. Nur-E-Kamal; Hiroshi Maruta, both of Victoria, Australia

[73] Assignee: Ludwig Institute for Cancer Research, New York, N.Y.

[21] Appl. No.: 510,284

[22] Filed: Aug. 2, 1995

Related U.S. Application Data

[63] Continuation of Ser. No. 71,575, Jun. 1, 1993, abandoned.
[51] Int. Cl.⁶ .................. C07K 14/00; C07K 14/435; C07K 14/47; C12N 15/12
[52] U.S. Cl. .................. 530/324; 530/350; 435/194; 435/69.1
[58] Field of Search .................. 514/2, 12; 530/300, 530/324, 350; 435/194

[56] References Cited

U.S. PATENT DOCUMENTS 5,227,292  7/1993  White ..................................... 435/69.1

OTHER PUBLICATIONS

Marchuk et al., "cDNA Cloning of the Type 1 Neurofibromatosis Gene: Complete Sequence of the NF1 Gene Product", Genomics 11: 931–940 (1991).

Japanese Biochemical Society Meeting (Oct. 1993) Maruta, H. et al.
Nur–E–Kamal et al., J. Biological Chemistry, vol. 268, No. 8, (Oct. 1993).
Martin, G. A. et al. Cell 63:843–849 (1990).
Wiesmuller, L. et al. J. Biol. Chem. 267:10207–10210 (1992).
Cawthon, R. M. et al. Cell 62:193–201 (1990).

*Primary Examiner*—Dian C. Jacobson
*Attorney, Agent, or Firm*—Felfe & Lynch

[57] ABSTRACT

This invention provides for a mechanism to reverse the activated Ras induced malignant transformation of mammalian cells by use of certain peptides. Specifically, the anti-oncogenic protein fragments of the Neurofibromatosis type 1 protein (NF1) were found to reverse, inhibit, or otherwise interfere with the malignant transformation of V-HaRas induced transformed cells. The invention further identifies several specific fragments of the NF1 protein which are capable of reversing activated Ras induced transformation, including the NF338, NF91, NF78 and NF56 protein fragments. The invention also provides for nucleic acid molecules, cell lines, and expression vectors associated with the NF1 fragments, in addition to protein complexes of the NF1 and Ras proteins. A method for screening molecules which are capable of reversing activated Ras induced transformation is also disclosed herein. Further described herein are pharmaceutical compositions containing the NF1 protein fragment or the nucleic acid molecules coding for the protein fragments. Methods for treating conditions characterized by activated Ras induced malignant transformation with the compositions.

7 Claims, 6 Drawing Sheets

5,580,955

FRAGMENTS OF NEUROFIBROMIN (NF1) AND METHOD TO REVERSE ACTIVATED RAS INDUCED MALIGNANT TRANSFORMATION IN MAMMALIAN CELLS

This application is a continuation, of application Ser. No. 08/071,575, filed Jun. 1, 1993, now abandoned.

FIELD OF THE INVENTION

This invention relates to the discovery that activated Ras induced malignant transformation can be reversed by fragments of neurofibromin (hereinafter "NF1"), the product of the Neurofibromatosis type I gene. A method for the expression of the NF1 fragments in mammalian cells is described herein, in addition to the polypeptides and nucleic acid molecules which are capable of reversing activated Ras induced transformation.

BACKGROUND OF THE INVENTION

The three functional Ras genes encode highly related proteins ($p21^{ras}$), of 188 or 189 amino acids. See generally Watson, Molecular Biology of the Gene, Fourth Edition, p.1065, et seq. After post-translational modification, the Ras proteins become associated with the inner surface of the plasma membrane. The Ras proteins are known to bind guanine nucleotides (GTP and GDP) and to possess GTPase activity. The GTP bound form of the Ras protein is the biologically active form, i.e. the signal transducing form. The hydrolysis of bound GTP to GDP results in the production of the inactive GDP bound form. Normal Ras proteins will remain in their inactive state until they receive a stimulus from an upstream exchange activity, which results in the exchange of GDP for GTP, followed by a change in the conformation of the Ras protein to its active state. The Ras proteins also have an intrinsic GTPase activity. This GTPase activity catalyzes the hydrolysis of GTP, which converts the active Ras protein to its inactive GDP-bound form.

It is believed that the Ras proteins play an essential role in the control of the mammalian cell cycle. In studies utilizing microinjection techniques, monoclonal antibodies against $p21^{ras}$ cause G1-induced arrested cell growth. Resting 3T3 cells injected with anti-Ras antibodies are unable to enter the S phase when they are stimulated to divide, while dividing 3T3 cells injected with the antibody are able to complete rounds of DNA synthesis in progress but fail to initiate new rounds.

The overexpression of $p21^{ras}$ has been shown to lead to transformation of certain cell-types. In addition, ras genes mutated at certain residues are also transforming. For instance, mutations in the gens leading to changes in the amino acid residues 12 and 61 can cause transformation. Also, mutations in the gens leading to the replacement of glycine with any amino acid except proline results in an activated or transforming gens. Activating mutations of p21 have been shown to result in the formation of increased levels of GTP-$p21^{ras}$, the active form.

Mutations in the Ras genes which lead to the formation of actived $p21^{ras}$ have been found in many tumor types, in particular pancreatic and colonic carcinomas where ras mutations are found in the majority of these tumor types, Bos, J. K. Cancer Research, 49, 4682–4689 (1989). This suggests that activated Ras genes may contribute to the development of tumors.

Neurofibromatosis is a common autosomal dominant disorder in humans. The protein encoded by a gene associated with Neurofibromatosis is termed NF1. The amino acid sequence of NF1 is set forth at SEQ ID NO: 1. It is a protein of 2818 amino acid residues, and has a 338 amino acid domain termed NF338 with 26% sequence identity with the C-terminal domain of a protein referred to as GAP1. The 709–1044 amino acid domain of GAP1 is known in the literature as "GAP1C". GAP, an acronym for "GTPase activating protein", refers to a class of proteins which have the ability to stimulate GTPase activity. Both GAP1 and NF1 have been shown to stimulate the normal Ras protein's GTPase activity. See Trahey, M. et al., Science, 238, 542–545 (1987); Vogel, U. S. et al., Nature 335, 90-39 (1988); Xu, G. et al., Cell 62, 599–609 (1990); Xu, G. et al., Cell 63,835–841 (1990); Martin, G. et al., Cell 63,848–849 (1990); and Marchuk, D. et al., Genomics 11, 931–940 (1991).

The instrinsic GTPase activity of the transforming mutants of $p21^{ras}$ is not activated by GAP1 or NF1. Therefore, oncogenic Ras mutants, such as V-HaRas, remain in an active form, i.e., the GTP bound form, for much longer periods than does normal Ras. As a result, these mutant ras proteins have more potent transforming activities than normal $p21^{ras}$.

There have been various attempts made to attenuate, inhibit, reverse, or otherwise interfere with the effects of ras transformation. In recent experiments, ras transformed NIH/3T3 cells have been tested with the hope of finding a cure and/or therapeutic approach to Ras-associated cancers. These attempts have included screening tumor suppressor genes which have been found to be able to reverse ras induced malignant transformation by DNA-mediated transfection and overexpression, as detailed in the following paragraph.

Several distinct tumor suppressor genes have been reported to reverse malignancy caused by the Ras oncogenes. See Contente, S. et al., Science 249, 796–798 (1990) and Buettner, R. et al., Mol. Cell. Biol. 11, 3573–3583 (1991): the full length human Rap1 (also called Krev1) which encodes a Ras related G protein of 184 amino acids, Kitayama, H. et al., Cell 56, 77–84 (1989), which tightly binds GAP1 but without any stimulation of its intrinsic GTPase activity, Hata Y, et al., J. Biol. Chem, 13, 265, 7104–7107 (1990); a truncated V-Jun encoding only the C-terminal domain of 150 amino acids (residues 147 to 296) which lacks the N-terminal transactivating domain, Lloyd A. et al., Nature 352, 635–638; the full length murine Thy-1 gene encoding a cell surface glycoprotein of 142 amino acids which is covalently linked to a glycophosphatidyl inositol, Sugimoto, Y. et al., Cancer Research, 51, 99–104 (1991); a human c-Ets-2 DNA encoding the C-terminal DNA-binding domain of 133 amino acids (residues 333 to 466) which binds to Ras responsive DNA element (RRE) in enhancers of several Ras-transactivated genes, Langer S. J. et al., Mol. Cell. Biol. 12, 5355–5362 (1992); and a rat B-myc DNA encoding the N-terminal DNA-binding domain of 120 amino acids which acts as a c-Myc antagonist, Resar, L. M. S. et al., Mol. Cell. Biol. 1130–1136 (1993). None of these gene products reverse transformation by binding directly to $p21^{ras}$.

All attempts to reverse malignant transformation caused by oncogenic Ras mutants with either the full length GAP1 or its C-terminal GTPase activating domain (GAP1C) have been unsuccessful, although GAP1C (but not full length GAP1) is able to reverse the malignant transformation caused by overexpression of normal $p21^{ras}$, Zhang, K. et al., Nature 346, 754–756 (1990). NF338 is also able to activate normal Ras GTPase activity, Wiesmueller, L. et al., J. Biol. Chem. 267, 10207–10210 (1992); Nur-E-Kamal M. S. A., et al., Mol. Biol. Cell, 3, 1437–1442 (1992) and was shown to bind the Ras protein much more tightly than the GAP1C, Martin, G. et al., Cell 63, 843–849 (1990). The NF338 fragment, which is similar but slightly larger than GAP1C, was reported to reduce the V-HaRas induced heat shock susceptibility of yeasts, Ballester, R. et al., Cell 63, 851–859 (1990).

Therefore a molecule that is capable of reversing or interfering with activated Ras induced malignant transformation was sought. It was discovered that a fragment of NF1 had the ability to attenuate, reverse or otherwise, interfere with Ras transformation. The overexpression of an NF1 fragment in V-HaRas transformed cells greatly reduced the cells' ability to form colonies in soft agar. This ability to form soft agar colonies is known to be closely associated with the cell's malignancy.

It was also found that the NF1 fragment's ability to reverse or interfere with activated Ras transformation was not based on the fragment's ability to act as a GTPase activating protein. Specifically, the NF56 fragment was found to be capable of reversing Ras transformation but is not capable of GTPase activation, as described in the discussion, infra.

Thus, it is the principal object of this invention to provide for a mechanism to reverse activated Ras transformation. The mechanism may include utilizing certain NF1 fragments which bind to $p21^{ras}$ to prevent interaction between the Ras protein and its downstream target.

Specifically, certain fragments of NF1, i.e., NF1 polypeptides and peptides, possess the ability to reverse Ras induced malignant transformation. The invention includes NF1 fragments and the isolated nucleic acid molecules which code for the fragments.

It is also an object of this invention to provide for expression vectors containing the nucleic acid molecules which code for such fragments of NF1.

It is a further object of this invention to provide for cells which are transfected with expression vectors containing nucleic acid molecules which code for fragments of NF1.

It is yet another object of this invention to provide for a protein complex containing the relevant NF1 fragments and all or part of a Ras protein.

Other objects of this invention include a method for reversing Ras induced transformation and a method for treating Ras induced conditions with pharmaceutical compositions containing the NF1 fragments, in addition to methods for determining whether other molecules are capable of reversing activated Ras induced transformation.

SUMMARY OF THE INVENTION

This invention generally provides for a mechanism to reverse Ras induced malignant transformation. Specifically, fragments of the neurofibromin (NF1) have been found to be capable of reversing activated Ras induced malignant transformation. Examples of these particular fragments include fragments of the neurofibromin, referred to as NF1. This invention also provides for the specific fragments of NF1 which reverse activated Ras induced malignant transformation. These fragments of NF1 include the NF338 protein fragment (amino acid residues 1194 to 1531), NF91 (amino acid residues 1441 to 1531), NF78 (amino acid residues 1441 to 1518), and NF56 (amino acid residues 1441 to 1496). Amino acid enumeration is made by way of reference to SEQ ID NO: 1.

This invention further provides for expression vectors containing the nucleic acid molecules which code for the NF1 fragments and mutants and which can be utilized to reverse transformation when the nucleic acid molecule is expressed or overexpressed.

Other inventions include the cells transfected by the expression vector, and method to screen peptides and other molecules capable of reversing Ras transformation.

DETAILED DESCRIPTION OF THE INVENTION

This invention will be better understood by reference to the following examples, which are included here for purposes of exemplification and are not to be construed as limitations.

EXAMPLE 1

Expression plasmids for expressing NF338 and NF91 were constructed.

Figure 1A:
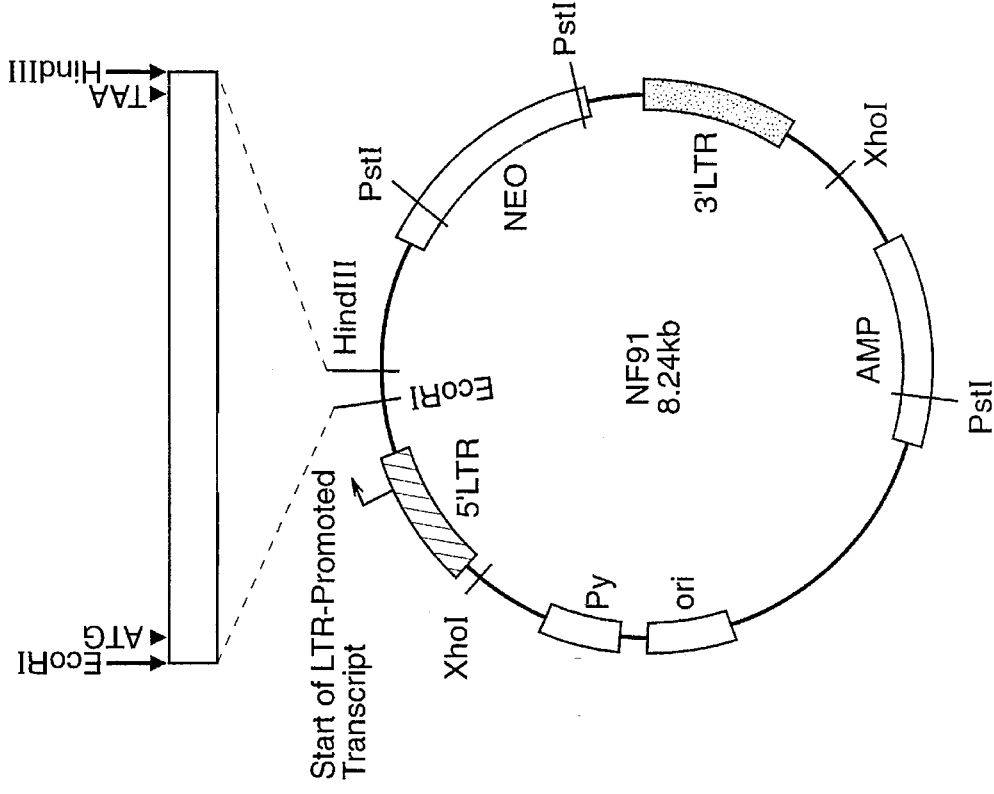
FIG. 1 Construction of plasmids NF338 and NF91.
Figure 1B:
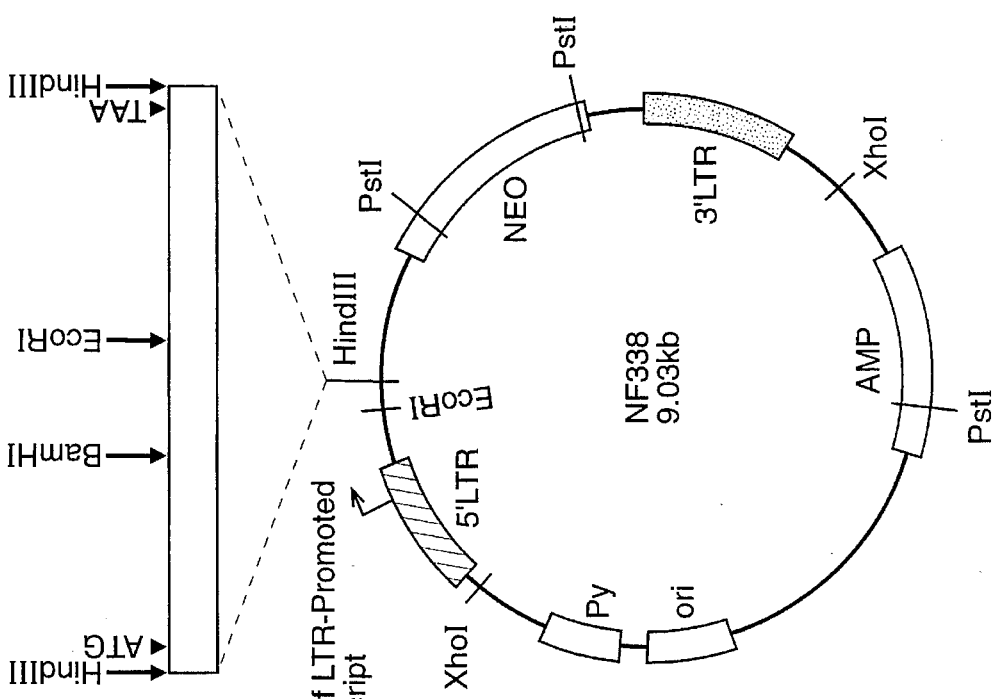
Figure 2A:
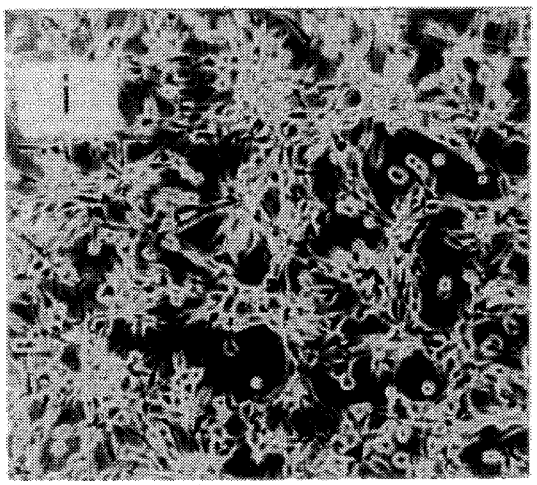
FIG. 2 Reversion of V-HaRas induced malignant transformation by overexpression of NF338 as shown by morphology of the cells and colony formation in soft agar.
Figure 2B:
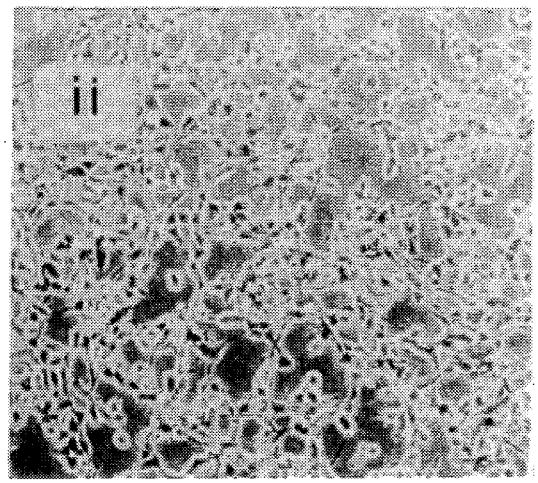
Figure 2C:
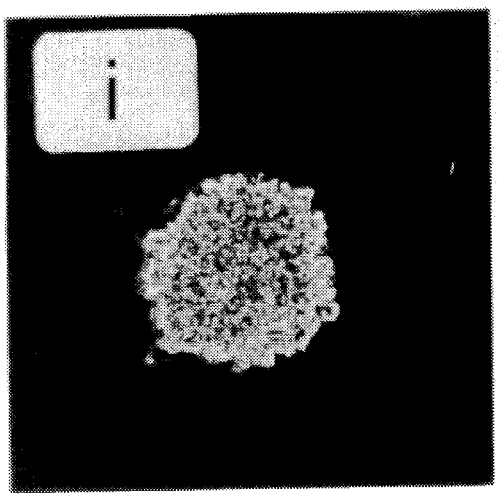
Figure 2D:
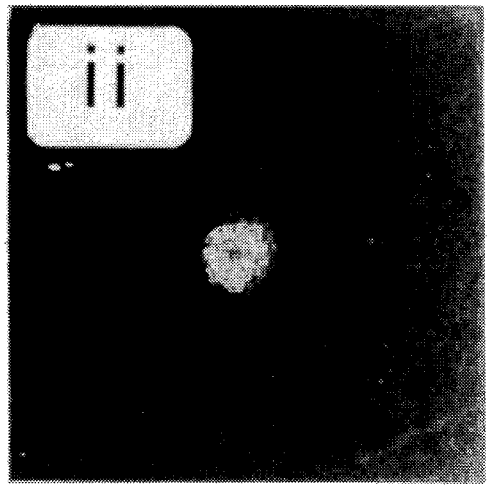

For NF338 expression, a HindIII DNA fragment of 1.1 kb containing a Kozak sequence (GCC GCC ACC ATG) at the 5' end, followed by codons 1194 to 1531 of human NF1 (type 1), and a termination codon (TAA) at the 3' end, was prepared and amplified using polymerase chain reaction and then subcloned into the retroviral vector pMV7. The pMV7 vector also contains neomycin and ampicillin resistance selectable markers, Kirschmeier, P. T. et al., DNA 7, 219–225 (1988). The orientation of the insert was determined by EcoRI digestion as one EcoRI site is located 100 base pairs upstream from the HindIII insertion site and the other at the codon 1355 of the NF1. See FIG. 1, panel A.

For the expression of NF91, an EcoRI/HindIII fragment of 0.3 kb containing the Kozak sequence at the 5' end followed by codons 1441 to 1531 of the human NF1 and the termination codon was prepared and amplified by PCR and then inserted into the EcoRI/HindIII sites of the vector pMV7. See FIG. 1, panel B. For the expression of NF78 and NF56, the corresponding EcoRI/HindIII fragments were subcloned in the manner similar to NF91.

The resultant plasmids, termed NF338, NF91, NF78 and NF56 were purified by $CsCl_2$ density gradient centrifugation, following well known techniques and were then used for transfection in the examples which follow.

Experiments using a protein vector prepared from *Pseudomonas exotoxin A* (PEA) were also conducted in a manner similar to the pMV7 vector (but not set forth herein). A description of the PEA protein vector can be found in Pastan, I, and Fitzgerald, O. J. Biol Chem, 264, 15157–15160 (1989), the disclosure of which is incorporated by reference in its entirety.

EXAMPLE 2

After the plasmids were constructed, transfection was carried out and the transfectants screened for expression of the sequence which codes for the NF1 fragments.

To test for transfection and efficacy, V-HaRas transformed NIH/3T3 cells, as described in Maruta, H., et al., J. Biol. Chem., 266, 11661–11668 (1991), the disclosure of which is incorporated by reference in its entirety, were first transfected with either NF338, NF91, NF78 or NF56 plasmids as complexes with liposomes (35 ug) as described previously in Maruta, H. et al., supra. and Nur-E-Kamal, M. S. A., et al., J. Biol. Chem. 267, 1415–1418 (1992), the disclosures of which are incorporated by reference in their entireties.

The transfectants were then cloned in the presence of a neomycin analogue, i.e., G418 at 400 ug/ml. The transfectants were initially screened for viability in the G418 medium, following Maruta et al., supra., and Nur-E.-Kamal et al., supra.

After the transfectants were screened for viability, the ability of the parental clone and each surviving transfectant to form soft agar colonies (SAC) were then examined by incubating 1000 cells per plate at 37° C. for three weeks under standard culture conditions, as described in Maruta et al., supra.

Unlike the normal NIH/3T3 cells, the majority of V-HaRas transformed cells expressing NF338 (sense) did not appear flat. Their morphology, however, differed significantly from that of the parental V-HaRas transformed NIH/3T3 cells. The morphology of (i) non-transfected cells (clone #0); and (ii) NF338 expressing cells (clone #22) were compared and the results set forth in panel A of FIG. 2.

The sense NF338 transfectant had greatly reduced ability to form soft agar colonies, in comparison to the non-transfected parent cells. The V-HaRas transformed NIH/3T3 cells were transfected with either NF338 or NF91, and the ability to form soft agar colonies was compared and the results set forth in panel B of FIG. 2 and the Table 1 below: (i) non-transfected cells (clone #0), (ii) NF338 expressing cells (clone #22). Further data on NF338 expressing cell (clone #8) and NF338 (antisense-clone #12) are set forth in Table 1 below.

TABLE 1

| Clone # | NF338 or NF91[a)] | Colonies/$10^3$ cells[b)] | SAC (%)[c)] |
|---|---|---|---|
| 0 | None | 735 (Large) | 100 |
| 8 | NF338 (Sense)[L] | 37 (medium) | 5 |
| 22 | NF338 (Sense)[H] | 3 (Small) | 0.4 |
| 12 | Anti-Sense[H] | 910 (Large) | 124 |
| 17 | NF91 (Sense)[H] | 0 (Flat)[d)] | 0 |

Figure 3A:
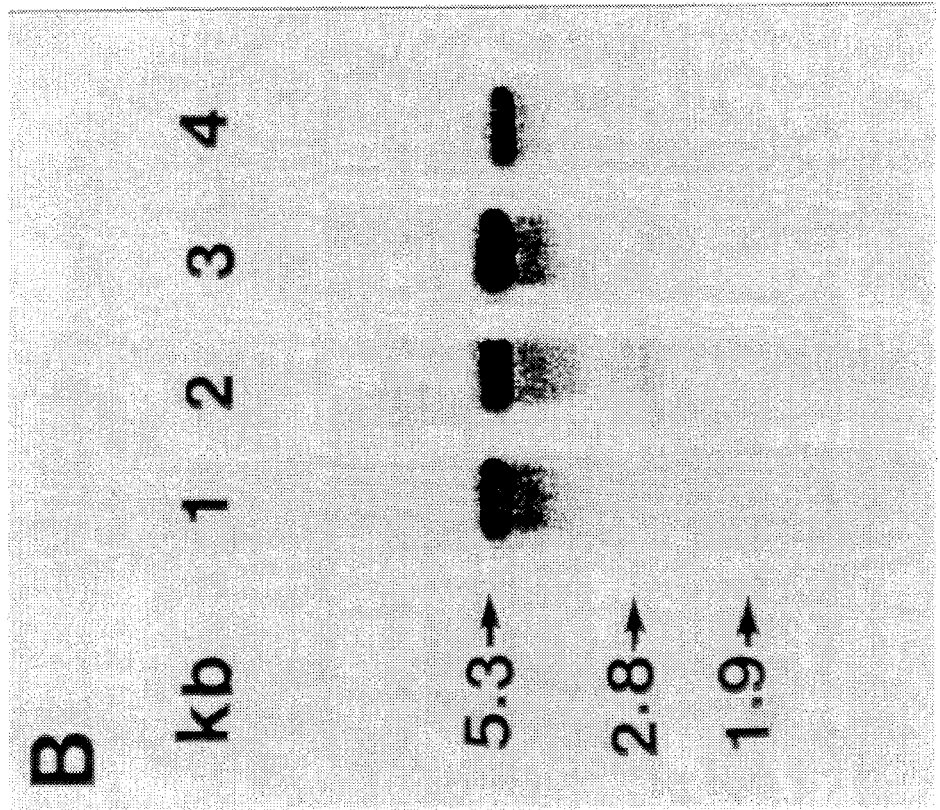
FIG. 3 Expression of NF338 (panel A) and V-HaRas (panel B) as determined by Northern blotting in transfected and non-transfected cells.
Figure 3B:
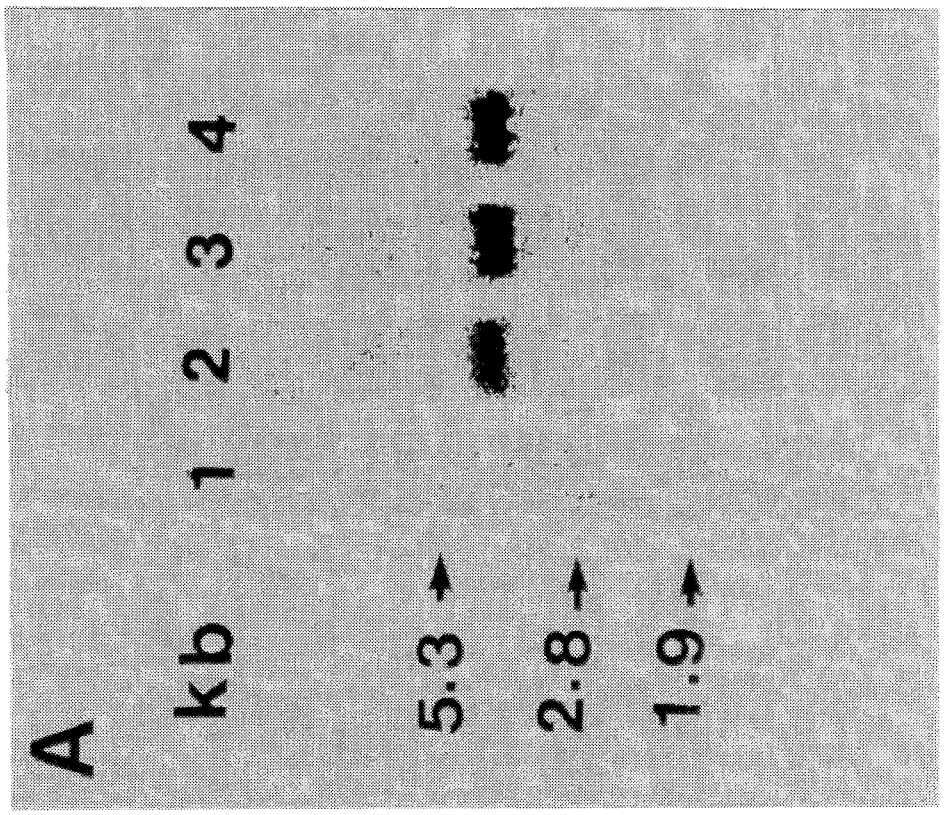
Figure 6:
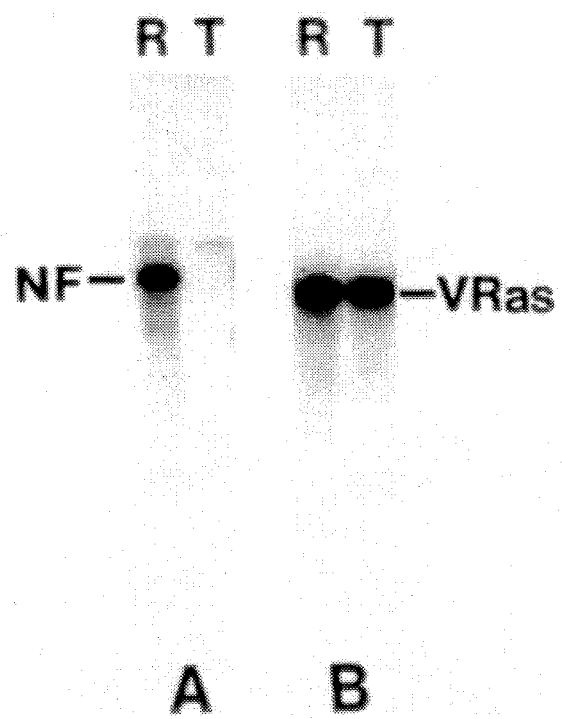
FIG. 6 Expression of NF91 and V-HaRas judged by Northern blotting in parental V-HaRas transformed cells and in V-HaRas transformed cells transfected with NF91.

KEY:
[a)]Relatively high (H) or low (L) steady-state levels of NF338 or NF91 mRNAs as judged by Northern blotting analysis, See panel A of FIG. 3 and FIG. 6.
[b)]the number of colonies found in soft agar whose average size of the colony is indicated in the parentheses ("Large" indicates consisting of more than 100 cells, "Medium" indicates consisting of approximately 25 cells, and "Small" indicates consisting of less than 10 cells per colony, See panel B of FIG. 2.
[c)]the relative soft agar colony (SAC) forming ability of each clone
[d)]the cell morphology of clone # 17 in liquid culture, See panel R of FIG. 5.

The clones 22 and 8 formed only 3 (small size) and 37 (medium size) colonies, respectively, whereas the parental V-HaRas transformed cells formed 735 (large size) colonies. Clone 12 which overexpressed antisense NF338 did not significantly differ from the parental cells in either its SAC, or its morphology, See Table 1 supra.

EXAMPLE 3

In addition to testing for SAC formation as a test of V-HaRas transformation, the clones were also subjected to Northern blot analysis for NF1 and V-HaRas mRNA expression.

From each clone, 5 ug of polyadenylated tail-containing mRNAs were isolated, and affinity-purified on an oligo (dT)-cellulose column using art recognized techniques. Each sample was separated by electrophoresis on a 1.2% agarose gel and transferred onto nitrocellulose filter paper, as described in Nur-E-Kamal et al., supra.

Hybridization probes were prepared by labelling either NF338 or V-HaRas DNAs, with [$\alpha^{32}p$] using a random labelling kit, (Bresatec Ltd. Australia) following the manufacturer's instructions. The specific activity of each DNA probe was approximately $10^9$ cpm/ug.

Northern hybridization was performed by blotting the filter with either NF338 or V-HaRas probes labelled with [$\alpha$-$^{32}$p] at 42° C. in the presence of formamide. The filters were subsequently washed at 30° C. with 2X SSC, as described in Maniatis et al., Molecular Cloning: A Laboratory Manual., pp. 447, Cold Spring Harbor, and washed twice with 0.1% sodium dodecyl sulfate (SDS) for 15 minutes and twice at 40° C. with 0.1X SSC plus 0.1% SDS for 15 minutes. The remaining probes on the filter were then scanned by a PhosphorImager™ -400 series (Molecular Dynamics, Ca.) or radioautographed.

There is good correlation between the sense NF338 mRNA levels and the extent of reduction in the formation of SAC, see panel A of FIG. 3 and Table 1. As determined by Northern analysis, the NF338 mRNA level of clone 22 was much higher than that of clone 8. Panels A and B of FIG. 3 show the expression of NF338 and V-HaRas, respectively, by the following clones: lane 1, non-transfected (clone #0); lane 2, sense NF338 transfected (clone #8); lane 3, sense NF338 transfected (clone #22); lane 4, antisense NF338 transfected (clone #12).

Furthermore, Northern analysis of V-HaRas mRNA confirmed that all transfectants still express the same type of V-HaRas as the parental cells, see panel B of FIG. 3, which indicates that the reduction in their oncogenicity is not due to the loss of V-HaRas expression, but is instead due to overexpression of NF338. This is the first demonstration of the ability of a protein fragment, which binds directly to the Ras protein, to interfere with the oncogenic action of Ras in mammalian cells.

EXAMPLE 4

To determine the minimum GTPase activating domain of NF1 and to screen for the smallest anti-oncogenic NF1 fragment, a series of GST fusion proteins containing truncated fragments of NF1 fragments were prepared.

Figure 4:
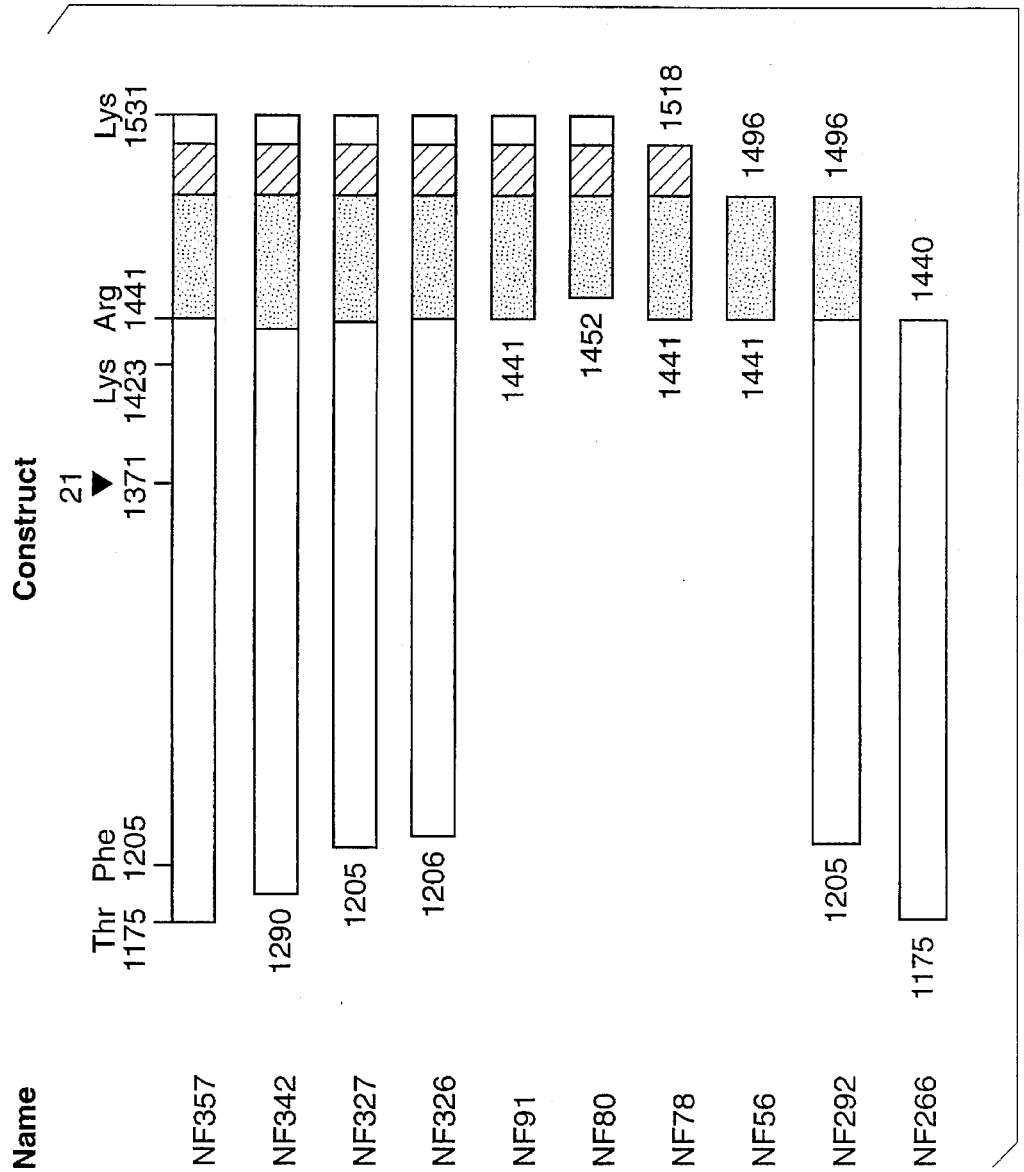
FIG. 4 N- and C- terminal deletion mutants of NF357 produced as GST fusion proteins.
Figure 5A:
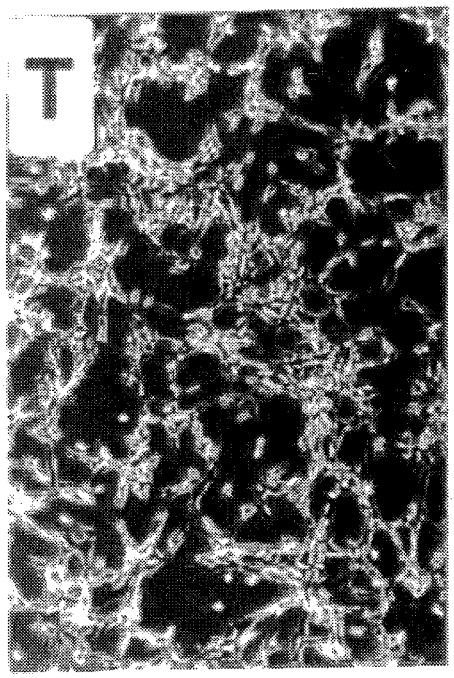
FIG. 5 Morphological change of V-HaRas transformed cells by overexpression of NF91.
Figure 5B:
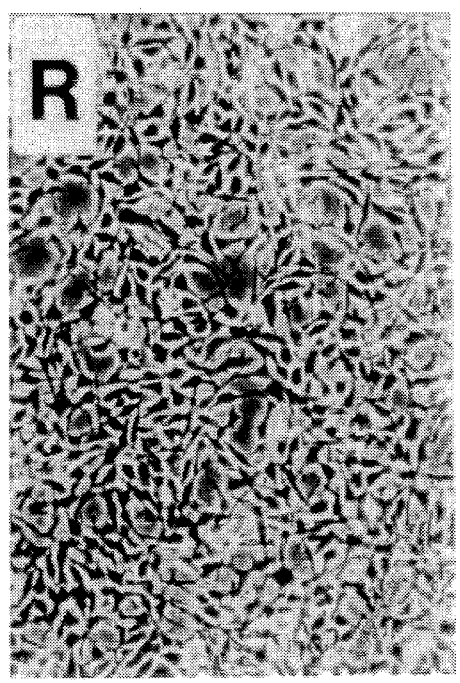
Figure 5C:
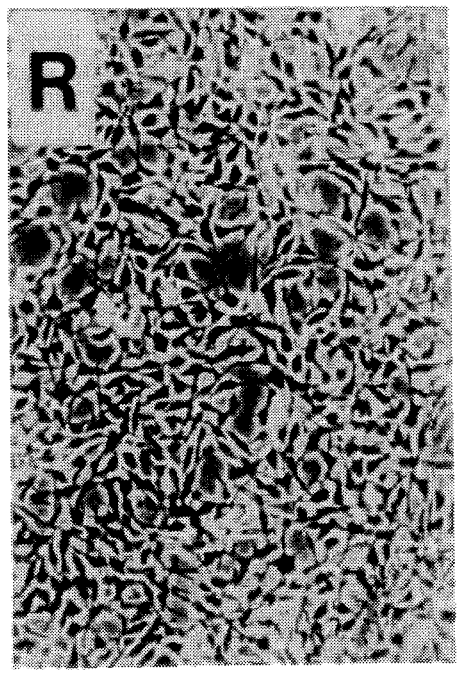
Figure 5D:

N- and C- terminal deletion mutants were constructed by subcloning the corresponding PCR DNA fragments into the bacterial expression vector pGEX-2TH, as described in Maruta et al., supra. FIG. 4 sets forth the DNA fragments inserted into the expression vector. The number following NF of each mutant indicates the total amino acid residues included. The DNA fragments inserted include the DNA for human type I NF357, human type II NF1-GRD (amino acid residues 1355 to 1531 in addition to the insert of 21 amino acids) and murine c-HaRas (residues 1–189). The type II-specific insert of 21 amino acids is indicated by the number 21 above a triangle following codon 1371. This 21 amino acid insert is set forth in SEQ ID NO: 2. The solid rectangle indicates the GAP active center of 56 amino acids, whereas the shaded rectangle indicates a supporting domain of 22 amino acids.

The expression vectors were transfected into *E.coli* and the protein expressed as GST fusion proteins. The fusion proteins were thereafter purified from *E.coli* as glutathione S-transfeRase fusion proteins and affinity-purified on a glutathione (GSH)-agarose column, as described in Maruta, et al., supra.

EXAMPLE 5

The purified proteins were then screened for Ras GTPase stimulating activity. The assay was carried out for each of the NF357 deletion mutants.

The hydrolysis of [gamma-$^{32}$P] GTP bound to c-HaRas protein was determined by incubating with bound protein at 25° C. for 20 minutes in the presence or absence of each NF1 mutant preparation in 100 ul of a buffer containing 50 mMTris-HCl, pH 7.5, 15 mMMgCl$_2$, 2.5 mM EDTA, 3 mM ATP, 1 mM dithiothreitol (DTT) and 0.5 mg/ml bovine serum albumin (BSA), then precipitating the unhydrolyzed [gamma-32P] GTP with charcoal, and finally measuring the radioactivity of the [gamma-32P] inorganic phosphate in the supernatant, as described previously, Maruta et al., supra. Protein concentrations were determined by the Bradford method with BSA as a standard.

As shown in Table II, the deletion of either its N-terminal 266 amino acids (residues 1175 to 1440) or its C-terminal 35 amino acids (residues 1497 to 1531) did not abolish Ras GTPase activation, although these mutations significantly reduced the efficiency of GTPase activation.

TABLE II

| NF1 Constructs[a] | Activation (fold)[b] | EC$_{50}$ (µg/ml)[c] |
| --- | --- | --- |
| NNF 357, 1175–1531 | 14 | 0.50 |
| NF 342, 1190–1531 | 14 | 0.52 |
| NF 327, 1205–1531 | 14 | 0.40 |
| NF 326, 1206–1531 | 11 | 1.5 |
| NF 91, 1441–1531 | 10 | 10 |
| NF 80, 1452–1531 | 0 | — |
| NF 78, 1441–1818 | 6 | 25 |
| NF 56, 1441–1496 | 0 | — |
| NF 292, 1205–1496 | 11 | 7.5 |
| NF 266, 1175–1440 | 0 | — |

[a]See FIG. 4 for detail of NF1 constructs
[b]Ras GTPase activation by 20 ug/ml NF1 mutants
[c]Concentrations required for 50% hydrolysis of GTP bound Ras.

The NF1 protein fragment of 91 amino acids (NF91, amino acid residues 1441 to 1531), still stimulated Ras GTPase activity, but was twenty times less efficient compared to NF342 of NF357. Further deletion of the N-terminal 11 amino acids (residues 1441–1451) completely abolished the GTPase activation. This suggests that the 56 amino acids (residues 1441–1496) of NF1 are sufficient for GTPase activation, and that some of the 11 amino acids (residues 1441 to 1451) are essential for its action.

However, the GST fusion protein containing only 56 amino acids of NF1, e.g., amino acid residues 1441 to 1496 (NF56), was no longer able to stimulate Ras GTPase activity, see FIG. 4 and Table II. The slightly larger NF1 fragment of 78 amino acids (residues 1441 to 1518) linked to GST was able to stimulate GTPase activation. It was also established that some of the 22 amino acids (residues 1497 to 1518) are functionally replaceable with the N-terminal 236 amino acids (residues 1205 to 1440) for the proper folding of NF56 or stability of its active site. This N-terminal domain alone did not show any GTPase activation, see Table II, supra., suggesting that its possible role is structural rather than functional.

EXAMPLE 6

As shown in example 5, NF91 (1441–1531) is still able to stimulate normal Ras GTPase activity, albeit its GAP activity is significantly reduced. This indicates that NF91 still binds to the Ras protein.

To examine if this domain still has anti-oncogenic activity in ras transformed cells, the Ras-binding domain of 91 amino acids (NF91) was overexpressed in the V-HaRas transformed NIH/3T3 cells by means of the vector pMV7, in a manner similar to example 2, supra.

Unlike the parental cells, many NF91 transfected clones became morphologically flat like the normal NIH/3T3 fibroblasts (see FIG. 5). The NF91 transfectants were also no longer able to form any soft agar colonies (see Table I). This suggests that NF91 is more potent than NF338 as a V-HaRas antagonist. FIG. 5 shows the morphological change of V-HaRas transformed cells by overexpression of NF91. T: V-HaRas transformed parental cells (clone #0), R: flat revertants (clone #17) derived from V-HaRas transformed cells transfected with the NF91, N: normal NIH/3T3 fibroblasts.

These observations suggest that NF91 is more anti-oncogenic than NF338 towards Ras transformed NIH/3T3 cells.

EXAMPLE 7

To prove whether the flat revertants express both NF91 and V-HaRas genes, the steady state levels of the corresponding mRNAs of the flat NF91 revertants and the parental cell lines were compared by Northern blot analysis. As shown in FIG. 6, the flat NF1 revertants still express the same type of V-HaRas as the parental cell line, whereas only the flat revertants expressed the NF91 gene. Panels A and B of FIG. 6, show the expression of NF91 and V-HaRas, respectively; T: V-HaRas transformed parental cells (clone #0), R: flat revertants (clone #17) derived from V-HaRas transformed cells transfected with NF91.

These observations indicate clearly that the loss of malignant phenotype is due to the overexpression of NF91 and not due to a loss of V-HaRas expression.

It is also of interest to note that NF91 is significantly smaller than the B-Myc N-terminal domain of 120 amino acids which, to date, is the smallest polypeptide known to reverse Ras induced malignant transformation, See Resar et al., Mol. Cell. Biol, 13, 1130–1136 (1993).

EXAMPLE 8

The NF91 revertants were also assayed for GTPase activity, following the protocol set forth in Example 5.

Comparing GTPase activity, NF357 is twenty times more active than NF91, (See Table II, supra.). These observations suggest, if not prove, that the poorer the protein is at stimulating Ras GTPase activity, the more potent an antioncogene it is, as long as the protein still binds to the Ras protein.

EXAMPLE 9

The transfectants expressing the smaller protein fragments, NF56 and NF78, were also assayed for GTPase activity, in a manner similar to Example 5.

It was found that the deletion of the C-terminal 13 amino acids from NF91 reduces its GTPase activity by 2.5 fold, while not abolishing GTPase activation (See Table II, NF78). Thus, it was of interest to examine if the remaining domain of 78 amino acids (NF78) is more potent as a Ras antagonist than NF91.

The deletion of the C-terminal 35 amino acids (residues 1497 to 1531) from NF357 still allowed the remaining domain to stimulate normal Ras GTPase activity (see Table II, NF292), suggesting that this C-terminal domain is not essential for the binding of NF357. However, the remaining domain of 56 amino acids (NF56) alone, produced by the deletion of non-essential N- and C-terminal domains (residues 1194–1440 and 1497–1531), is no longer able to stimulate Ras GTPase activity (see Table II, NF56).

However expression of the NF56 fragment (residues 1441 to 1496) is still leads to reversion of activated Ras induced transformation as determined by using the assays described supra. Since NF56 cannot stimulate either normal Ras GTPase activity or its oncogenic mutants, its anti-activated Ras action is not due to GTP to GDP conversion of activated Ras but probably due to its tight binding to the Ras protein, thereby preventing the Ras protein from interacting with a downstream target.

EXAMPLE 10

Experiments, which are summarized below, were carried out to determine the importance of specific amino acid residues. The amino acid sequences were manipulated, i.e., deletion or replacement of specific amino acid residues, according to well-known techniques. Since the deletion of the N-terminal 236 amino acids (residues 1205–1440) significantly reduced the efficiency of the GTPase activation, the amino acid residue or residues that play a key role in maximizing GTPase activation were identified.

It was determined that deletion of $Phe^{1205}$ (or its replacement by Ser) alone significantly reduced the GTPase activation of the NF327 (amino acid residues 1206–1531), See FIG. 4, Table II. This suggests that $Phe^{1205}$ plays an important role in maximizing GTPase activation.

In comparison to the GAP1C molecule, the corresponding residue ($Tyr^{720}$) also appears to play a key role in GTPase activation. Although replacement of $Tyr^{720}$ by either Phe or Leu does not affect GTPase activation, either $Glu^{720}$ or $Gly^{720}$ mutations almost completely abolish it. These observations suggest that a hydrophobic residue (Tyr, Phe or Leu) is required at position 720 of the GAP1C or at position 1205 of NF1 for full stimulation of the Ras GTPase activity.

Further deletion of 235 amino acids (residues 1206 to 1440) from NF326 also significantly reduced GTPase activation, see FIG. 4 and Table II, indicating that some of these amino acids are involved in stimulation of GTPase activity by NF91, and NF56, which does not stimulate GTPase activity, when used alone.

It is of interest to note that the GTPase activating NF1 fragment of 78 amino acids (NF78) shares only 19% sequence identity with the corresponding domain of GAP1, which is totally inactive. Surprisingly, this sequence identity is even lower than that (26%) between the active GAP1C (residues 720 to 1044) and the corresponding NF1-GRD. Furthermore, although the GAP1C is completely inactivated by either freezing/thawing or storage at 4° C. for 6 months, the GAP activity of both the corresponding NF1-GRD and even NF78 is not significantly affected by these treatment/ storage conditions. These observations suggest that the NF1-GRD and NF78 are significantly different from the corresponding domains of GAP1 in either the overall conformation or stability of the active site.

As discussed in Li Y. et al., Cell 69, 275–281 (1992), replacement of $Lys^{1423}$ by either a Glu or Gln in NF1 almost completely abolishes its ability to stimulate the GTPase activity of the Ras protein which suggests that this residue plays an important role in GTPase activation. However, the $Met^{1423}$ mutation only converts NF1 to a temperature-sensitive (ts) molecule, but does not significantly affect its GTPase activation, Wiesmueller, supra. This suggests that $Lys^{1423}$ may be involved in stabilization of the NF1, but is not essential for GTPase activation.

It has been demonstrated by the above that either NF78 or NF91 (residues 1441 or 1518 to 1531) which lack $Lys^{1423}$ are still able to stimulate Ras GTPase activity, clearly indicating that the Lys residue is localized outside the GTPase activating domain of NF1.

The discovery that certain NF1 fragments are capable of reversing activated Ras induced transformation has tremendous potential in providing a therapy to attentuate Ras related tumors.

The NF1 fragments, i.e., polypeptide and peptides, are provided herein, in addition to the nucleic acid molecules which code for the protein fragments. The expression vectors containing the nucleic acid molecules are also provided herein. The vectors are operably linked to at least one promoter, i.e. an LTR promoter or other suitable promoters, and which contain proteins conferring ampicillin and neomycin resistance. The vector can also be a plasmid.

Further provided herein are the cells or cell lines which may be used to transfect the expression vector, where the cells can be derived from eukaryotic and mammalian cells. Specifically, the NIH/3T3 cell line transfected with NF1 protein fragment is one example.

In addition, the protein complex containing both Ras and NF1 fragments is also provided herein. The protein complex will consist of a first molecule having an amino acid sequence corresponding to at least a portion of the NF1 protein and a second molecule having an amino acid sequence corresponding to at least a portion of the Ras protein.

This invention also provides for a method to reverse activated Ras induced malignant transformation by transfecting a vector having the nucleic acid molecule coding for the NF1 protein fragment into a Ras induced transformed cell and culturing the transfected Ras transformed cell under conditions which would be appropriate for overexpression of the protein fragment to a level sufficient to reverse the activated Ras induced malignant transformation.

Another aspect of the invention is a pharmaceutical formulation comprising an NF1 fragment formulated for pharmaceutical use, optionally together with an acceptable adjuvant, diluent, carrier or excipient and/or in unit dosage form. Conventional pharmaceutical practice may be employed to provide suitable formulations or compositions.

Thus, the formulations of this invention can be applied to parenteral administration, for example, intravenous, subcutaneous, intramuscular, intraorbital, opthalmic, intraventricular, intracranial, intracapsular, intRaspinal, intracisternal, intraperitoneal, topical, intranasal, aerosol, scarification, and also oral, buccal, rectal or vaginal administration.

The formulations of this invention may also be administered by the transplantation into the patient of host cells expressing the nucleic acid molecules of the instant invention or by the use of surgical implants which release the formulations of the invention. The transplantation can also be performed at the specific tumor site.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences."

In general terms, the NF1 protein fragments of this invention may be provided in an aqueous physiological buffer solution containing about 0.1 to 10% w/v compound for parenteral administration. General dose ranges are from about 1 mg/kg to about 1 g/kg of body weight per day; a preferred dose range is from about 0.01 mg/kg to 100 mg/kg of body weight per day. The preferred dosage to be administered is likely to depend upon the type and extent of progression of the condition being addressed, the overall health of the patient, the make up of the formulation, and the route of administration.

A further aspect of the invention useful for treating activated Ras induced malignant transformation, is a pharmaceutical composition comprising a nucleic acid molecule which codes for the NF1 peptide. The composition also contains a carrier which facilitates the incorporation of the nucleic acid molecule into the activated Ras transformed cell. Examples of suitable carriers include any material which is capable of "carrying" the nucleic acid molecule into the cell, i.e. which facilitates the nucleic acid molecule's entry into the cell, to alter the transformed cell. A specific example of a suitable carrier is a liposome which can encapsulate the nucleic acid molecule for transport into the cell. Other specific examples of carriers can be readily determined by those skilled in the art.

The invention can also be used to screen molecules for the ability to reverse activated Ras induced malignant transformation. This method entails contacting a known amount of the NF1 fragment and an amount of the sample with activated Ras protein and measuring the binding of the NF1 fragment to the Ras protein. Once a molecule has been identified to interfere with the binding of the NF1 fragment to the Ras protein, the molecule is contacted with Ras transformed cells and the cells are screened for signs of reversion. These tests can include the ability to form soft agar colonies, as described previously.

The study of the structure of the protein complexes of NF1 and Ras using art known techniques can lead to the design of molecules which mimic the action of the NF1 fragments.

Certain molecules which can act as antagonists for the Ras protein are also provided herein. An antagonist which competes with the NF1 fragment for binding to the Ras protein is also intended, provided that the antagonist is not an antibody.

It is believed that other embodiments may be incorporated into the present invention without departing from the spirit and scope of the invention. It is not intended that the present invention be limited to only the described embodiments. Modification of these embodiments will be recognized by those skilled in the art. Rather, the invention should be circumscribed by the scope of the appended claims.

We claim:

1. Isolated polypeptide which consists of an amino acid sequence which begins with one of amino acids 1175–1441 of NF1 and ends with one of amino acids 1496–1531 of NF1 as set forth in SEQ ID NO: 1.

2. Isolated polypeptide of claim 1, wherein said NF1 polypeptide is an NF1 type I isoform.

3. Isolated polypeptide of claim 1, consisting of amino acid 1194 to amino acid 1531 of NF1 as set forth in SEQ ID NO: 1.

4. Isolated polypeptide of claim 1, consisting of amino acid 1441 to amino acid 1531 of NF1 as set forth in SEQ ID NO: 1.

5. Isolated polypeptide of claim 1, consisting of amino acid 1441 to amino acid 1518 of NF1 as set forth in SEQ. ID. NO: 1.

6. Isolated polypeptide of claim 1, consisting of amino acid 1441 to amino acid 1496 of NF1 as set forth in SEQ ID NO: 1.

7. Isolated polypeptide which consists of an amino acid sequence which begins with amino acids 1355–1370 of SEQ ID NO: 1, is followed by amino acids 1–21 of SEQ ID NO: 2, and ends with amino acids 1371–1531 of SEQ ID NO: 1.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 2818 amino acids
        ( B ) TYPE: amino acid
        ( D ) TOPOLOGY: linear ( i i ) MOLECULE TYPE: protein ( x ) PUBLICATION INFORMATION:
        ( A ) AUTHORS: Marchuk, Douglas A.; Saulino, Ann M.;
            Tavakkol, Roxanne; Swaroop, Manju;
            Wallace, Magaret R.; Andersen, Lone B.;
            Mitchell, Anna L.; Gutmann, David H.;
            Boguski, Mark; Collins, Francis S.
        ( B ) TITLE: cDNA Cloning of the Type 1 Neurofibromatosis Gene:
            Complete Sequence of the NF1 Gene Product
        ( C ) JOURNAL: Genomics
        ( D ) VOLUME: 11
        ( E ) PAGES: 931-940
        ( F ) DATE: 1991

( x i ) SEQUENCE DESCRIPTION: SEQ ID NO: 1:

Met Ala Ala His Arg Pro Val Glu Trp Val Gln Ala Val Val Ser Arg
                5                      10                    15

```
Phe  Asp  Glu  Gln  Leu  Pro  Ile  Lys  Thr  Gly  Gln  Gln  Asn  Thr  His  Thr
               20                  25                      30

Lys  Val  Ser  Thr  Glu  His  Asn  Lys  Glu  Cys  Leu  Ile  Asn  Ile  Ser  Lys
               35                  40                      45

Tyr  Lys  Phe  Ser  Leu  Val  Ile  Ser  Gly  Leu  Thr  Thr  Ile  Leu  Lys  Asn
     50                       55                 60

Val  Asn  Asn  Met  Arg  Ile  Phe  Gly  Glu  Ala  Ala  Glu  Lys  Asn  Leu  Tyr
65                       70                      75                            80

Leu  Ser  Gln  Leu  Ile  Ile  Leu  Asp  Thr  Leu  Glu  Lys  Cys  Leu  Ala  Gly
               85                       90                            95

Gln  Pro  Lys  Asp  Thr  Met  Arg  Leu  Asp  Glu  Thr  Met  Leu  Val  Lys  Gln
               100                 105                     110

Leu  Leu  Pro  Glu  Ile  Cys  His  Phe  Leu  His  Thr  Cys  Arg  Glu  Gly  Asn
               115                 120                     125

Gln  His  Ala  Ala  Glu  Leu  Arg  Asn  Ser  Ala  Ser  Gly  Val  Leu  Phe  Ser
     130                      135                     140

Leu  Ser  Cys  Asn  Asn  Phe  Asn  Ala  Val  Phe  Ser  Arg  Ile  Ser  Thr  Arg
145                      150                     155                           160

Leu  Gln  Glu  Leu  Thr  Val  Cys  Ser  Glu  Asp  Asn  Val  Asp  Val  His  Asp
               165                 170                     175

Ile  Glu  Leu  Leu  Gln  Tyr  Ile  Asn  Val  Asp  Cys  Ala  Lys  Leu  Lys  Arg
               180                 185                     190

Leu  Leu  Lys  Glu  Thr  Ala  Phe  Lys  Phe  Lys  Ala  Leu  Lys  Lys  Val  Ala
               195                 200                     205

Gln  Leu  Ala  Val  Ile  Asn  Ser  Leu  Glu  Lys  Ala  Phe  Trp  Asn  Trp  Val
     210                      215                     220

Glu  Asn  Tyr  Pro  Asp  Glu  Phe  Thr  Lys  Leu  Tyr  Gln  Ile  Pro  Gln  Thr
225                      230                     235                           240

Asp  Met  Ala  Glu  Cys  Ala  Glu  Lys  Leu  Phe  Asp  Leu  Val  Asp  Gly  Phe
               245                 250                     255

Ala  Glu  Ser  Thr  Lys  Arg  Lys  Ala  Ala  Val  Trp  Pro  Leu  Gln  Ile  Ile
               260                 265                     270

Leu  Leu  Ile  Leu  Cys  Pro  Glu  Ile  Ile  Gln  Asp  Ile  Ser  Lys  Asp  Val
               275                 280                     285

Val  Asp  Glu  Asn  Asn  Met  Asn  Lys  Lys  Leu  Phe  Leu  Asp  Ser  Leu  Arg
     290                      295                     300

Lys  Ala  Leu  Ala  Gly  His  Gly  Gly  Ser  Arg  Gln  Leu  Thr  Glu  Ser  Ala
305                      310                     315                           320

Ala  Ile  Ala  Cys  Val  Lys  Leu  Cys  Lys  Ala  Ser  Thr  Tyr  Ile  Asn  Trp
               325                 330                     335

Glu  Asp  Asn  Ser  Val  Ile  Phe  Leu  Leu  Val  Gln  Ser  Met  Val  Val  Asp
               340                 345                     350

Leu  Lys  Asn  Leu  Leu  Phe  Asn  Pro  Ser  Lys  Pro  Phe  Ser  Arg  Gly  Ser
          355                 360                     365

Gln  Pro  Ala  Asp  Val  Asp  Leu  Met  Ile  Asp  Cys  Leu  Val  Ser  Cys  Phe
     370                      375                     380

Arg  Ile  Ser  Pro  His  Asn  Asn  Gln  His  Phe  Lys  Ile  Cys  Leu  Ala  Gln
385                      390                     395                           400

Asn  Ser  Pro  Ser  Thr  Phe  His  Tyr  Val  Leu  Val  Asn  Ser  Leu  His  Arg
               405                 410                     415

Ile  Ile  Thr  Asn  Ser  Ala  Leu  Asp  Trp  Trp  Pro  Lys  Ile  Asp  Ala  Val
               420                 425                     430

Tyr  Cys  His  Ser  Val  Glu  Leu  Arg  Asn  Met  Phe  Gly  Glu  Thr  Leu  His
               435                 440                     445
```

```
Lys  Ala  Val  Gln  Gly  Cys  Gly  Ala  His  Pro  Ala  Ile  Arg  Met  Ala  Pro
     450                 455                 460
Ser  Leu  Thr  Phe  Lys  Glu  Lys  Val  Thr  Ser  Leu  Lys  Phe  Lys  Glu  Lys
465                      470                 475                           480
Pro  Thr  Asp  Leu  Glu  Thr  Arg  Ser  Tyr  Lys  Tyr  Leu  Leu  Leu  Ser  Met
                    485                      490                      495
Val  Lys  Leu  Ile  His  Ala  Asp  Pro  Lys  Leu  Leu  Leu  Cys  Asn  Pro  Arg
               500                 505                      510
Lys  Gln  Gly  Pro  Glu  Thr  Gln  Gly  Ser  Thr  Ala  Glu  Leu  Ile  Thr  Gly
          515                      520                      525
Leu  Val  Gln  Leu  Val  Pro  Gln  Ser  His  Met  Pro  Glu  Ile  Ala  Gln  Glu
     530                     535                      540
Ala  Met  Glu  Ala  Leu  Leu  Val  Leu  His  Gln  Leu  Asp  Ser  Ile  Asp  Leu
545                      550                      555                      560
Trp  Asn  Pro  Asp  Ala  Pro  Val  Glu  Thr  Phe  Trp  Glu  Ile  Ser  Ser  Gln
                    565                      570                      575
Met  Leu  Phe  Tyr  Ile  Cys  Lys  Lys  Leu  Thr  Ser  His  Gln  Met  Leu  Ser
               580                      585                      590
Ser  Thr  Glu  Ile  Leu  Lys  Trp  Leu  Arg  Glu  Ile  Leu  Ile  Cys  Arg  Asn
          595                      600                      605
Lys  Phe  Leu  Leu  Lys  Asn  Lys  Gln  Ala  Asp  Arg  Ser  Ser  Cys  His  Phe
     610                     615                      620
Leu  Leu  Phe  Tyr  Gly  Val  Gly  Cys  Asp  Ile  Pro  Ser  Ser  Gly  Asn  Thr
625                      630                      635                      640
Ser  Gln  Met  Ser  Met  Asp  His  Glu  Glu  Leu  Leu  Arg  Thr  Pro  Gly  Ala
               645                      650                      655
Ser  Leu  Arg  Lys  Gly  Lys  Gly  Asn  Ser  Ser  Met  Asp  Ser  Ala  Ala  Gly
          660                      665                      670
Cys  Ser  Gly  Thr  Pro  Pro  Ile  Cys  Arg  Gln  Ala  Gln  Thr  Lys  Leu  Glu
          675                      680                      685
Val  Ala  Leu  Tyr  Met  Phe  Leu  Trp  Asn  Pro  Asp  Thr  Glu  Ala  Val  Leu
     690                     695                      700
Val  Ala  Met  Ser  Cys  Phe  Arg  His  Leu  Cys  Glu  Glu  Ala  Asp  Ile  Arg
705                      710                      715                      720
Cys  Gly  Val  Asp  Glu  Val  Ser  Val  His  Asn  Leu  Leu  Pro  Asn  Tyr  Asn
                    725                      730                      735
Thr  Phe  Met  Glu  Phe  Ala  Ser  Val  Ser  Asn  Met  Met  Ser  Thr  Gly  Arg
               740                      745                      750
Ala  Ala  Leu  Gln  Lys  Arg  Val  Met  Ala  Leu  Leu  Arg  Arg  Ile  Glu  His
          755                      760                      765
Pro  Thr  Ala  Gly  Asn  Thr  Glu  Ala  Trp  Glu  Asp  Thr  His  Ala  Lys  Trp
     770                     775                      780
Glu  Gln  Ala  Thr  Lys  Leu  Ile  Leu  Asn  Tyr  Pro  Lys  Ala  Lys  Met  Glu
785                      790                      795                      800
Asp  Gly  Gln  Ala  Ala  Glu  Ser  Leu  His  Lys  Thr  Ile  Val  Lys  Arg  Arg
                    805                      810                      815
Met  Ser  His  Val  Ser  Gly  Gly  Gly  Ser  Ile  Asp  Leu  Ser  Asp  Thr  Asp
               820                      825                      830
Ser  Leu  Gln  Glu  Trp  Ile  Asn  Met  Thr  Gly  Phe  Leu  Cys  Ala  Leu  Gly
          835                      840                      845
Gly  Val  Cys  Leu  Gln  Gln  Arg  Ser  Asn  Ser  Gly  Leu  Ala  Thr  Tyr  Ser
     850                     855                      860
Pro  Pro  Met  Gly  Pro  Val  Ser  Glu  Arg  Lys  Gly  Ser  Met  Ile  Ser  Val
```

-continued

| 865 | | | | 870 | | | | 875 | | | | 880 | | | |
|---|---|---|---|---|---|---|---|---|---|---|---|---|---|---|---|
| Met | Ser | Ser | Glu | Gly | Asn | Ala | Asp | Thr | Pro | Val | Ser | Lys | Phe | Met | Asp |
| | | | | 885 | | | | 890 | | | | 895 | | | |
| Arg | Leu | Leu | Ser | Leu | Met | Val | Cys | Asn | His | Glu | Lys | val | Gly | Leu | Gln |
| | | | 900 | | | | | 905 | | | | | 910 | | |
| Ile | Arg | Thr | Asn | Val | Lys | Asp | Val | Gly | Leu | Glu | Leu | Ser | Pro | Ala | |
| | | 915 | | | | 920 | | | | | 925 | | | | |
| Leu | Tyr | Pro | Met | Leu | Phe | Asn | Lys | Leu | Lys | Asn | Thr | Ile | Ser | Lys | Phe |
| | 930 | | | | | 935 | | | | | 940 | | | | |
| Phe | Asp | Ser | Gln | Gly | Gln | Val | Leu | Leu | Thr | Thr | Asn | Thr | Gln | Phe | |
| 945 | | | | | 950 | | | | | 955 | | | | 960 | |
| Val | Glu | Gln | Thr | Ile | Ala | Ile | Met | Lys | Asn | Leu | Leu | Asp | Asn | His | Thr |
| | | | | 965 | | | | | 970 | | | | | 975 | |
| Glu | Gly | Ser | Ser | Glu | His | Leu | Gly | Gln | Ala | Ser | Ile | Glu | Thr | Met | Met |
| | | | 980 | | | | | 985 | | | | | 990 | | |
| Leu | Asn | Leu | Val | Arg | Tyr | Val | Arg | Val | Leu | Gly | Asn | Met | Val | His | Ala |
| | | | 995 | | | | 1000 | | | | | 1005 | | | |
| Ile | Gln | Ile | Lys | Thr | Lys | Leu | Cys | Gln | Leu | Val | Glu | Val | Met | Met | Ala |
| | | 1010 | | | | | 1015 | | | | | 1020 | | | |
| Arg | Arg | Asp | Asp | Leu | Ser | Phe | Cys | Gln | Glu | Met | Lys | Phe | Arg | Asn | Lys |
| 1025 | | | | | 1030 | | | | | 1035 | | | | | 1040 |
| Met | Val | Glu | Tyr | Leu | Thr | Asp | Trp | Val | Met | Gly | Thr | Ser | Asn | Gln | Ala |
| | | | | 1045 | | | | | 1050 | | | | | 1055 | |
| Ala | Asp | Asp | Asp | Val | Lys | Cys | Leu | Thr | Arg | Asp | Leu | Asp | Gln | Ala | Ser |
| | | | 1060 | | | | | 1065 | | | | | 1070 | | |
| Met | Glu | Ala | Val | Val | Ser | Leu | Leu | Ala | Gly | Leu | Pro | Leu | Gln | Pro | Glu |
| | | | 1075 | | | | | 1080 | | | | | 1085 | | |
| Glu | Gly | Asp | Gly | Val | Glu | Leu | Met | Glu | Ala | Lys | Ser | Gln | Leu | Phe | Leu |
| | | | 1090 | | | | | 1095 | | | | | 1100 | | |
| Lys | Tyr | Phe | Thr | Leu | Phe | Met | Asn | Leu | Leu | Asn | Asp | Cys | Ser | Glu | Val |
| 1105 | | | | | 1110 | | | | | 1115 | | | | | 1120 |
| Glu | Asp | Glu | Ser | Ala | Gln | Thr | Gly | Gly | Arg | Lys | Arg | Gly | Met | Ser | Arg |
| | | | | 1125 | | | | | 1130 | | | | | 1135 | |
| Arg | Leu | Ala | Ser | Leu | Arg | His | Cys | Thr | Val | Leu | Ala | Met | Ser | Asn | Leu |
| | | | 1140 | | | | | 1145 | | | | | 1150 | | |
| Leu | Asn | Ala | Asn | Val | Asp | Ser | Gly | Leu | Met | His | Ser | Ile | Gly | Leu | Gly |
| | | | 1155 | | | | | 1160 | | | | | 1165 | | |
| Tyr | His | Lys | Asp | Leu | Gln | Thr | Arg | Ala | Thr | Phe | Met | Glu | Val | Leu | Thr |
| | | | 1170 | | | | | 1175 | | | | | 1180 | | |
| Lys | Ile | Leu | Gln | Gln | Gly | Thr | Glu | Phe | Asp | Thr | Leu | Ala | Glu | Thr | Val |
| 1185 | | | | | 1190 | | | | | 1195 | | | | | 1200 |
| Leu | Ala | Asp | Arg | Phe | Glu | Arg | Leu | Val | Glu | Leu | Val | Thr | Met | Met | Gly |
| | | | | 1205 | | | | | 1210 | | | | | 1215 | |
| Asp | Gln | Gly | Glu | Leu | Pro | Ile | Ala | Met | Ala | leu | Ala | Asn | Val | Val | Pro |
| | | | | 1220 | | | | | 1225 | | | | | 1230 | |
| Cys | Ser | Gln | Trp | Asp | Glu | Leu | Ala | Arg | Val | Leu | Val | Thr | Leu | Phe | Asp |
| | | | 1235 | | | | | 1240 | | | | | 1245 | | |
| Ser | Arg | His | Leu | Leu | Tyr | Gln | Leu | Leu | Trp | Asn | Met | Phe | Ser | Lys | Glu |
| | 1250 | | | | | 1255 | | | | | 1260 | | | | |
| Val | Glu | Leu | Ala | Asp | Ser | Met | Gln | Thr | Leu | Phe | Arg | Gly | Asn | Ser | Leu |
| 1265 | | | | | 1270 | | | | | 1275 | | | | | 1280 |
| Ala | Ser | Lys | Ile | Met | Thr | Phe | Cys | Phe | Lys | Val | Tyr | Gly | Ala | Thr | Tyr |
| | | | | 1285 | | | | | 1290 | | | | | 1295 | |

-continued

Leu Gln Lys Leu Leu Asp Pro Leu Leu Arg Ile Val Ile Thr Ser Ser
            1300                1305                1310
Asp Trp Gln His Val Ser Phe Glu Val Asp Pro Thr Arg Leu Glu Pro
        1315                1320                1325
Ser Glu Ser Leu Glu Glu Asn Gln Arg Asn Leu Leu Gln Met Thr Glu
    1330                1335                1340
Lys Phe Phe His Ala Ile Ile Ser Ser Ser Ser Glu Phe Pro Pro Gln
1345                1350                1355                1360
Leu Arg Ser Val Cys His Cys Leu Tyr Gln Val Val Ser Gln Arg Phe
                1365                1370                1375
Pro Gln Asn Ser Ile Gly Ala Val Gly Ser Ala Met Phe Leu Arg Phe
            1380                1385                1390
Ile Asn Pro Ala Ile Val Ser Pro Tyr Glu Ala Gly Ile Leu Asp Lys
            1395                1400                1405
Lys Pro Pro Pro Arg Ile Glu Arg Gly Leu Lys Leu Met Ser Lys Ile
    1410                1415                1420
Leu Gln Ser Ile Ala Asn His Val Leu Phe Thr Lys Glu Glu His Met
1425                1430                1435                1440
Arg Pro Phe Asn Asp Phe Val Lys Ser Asn Phe Asp Ala Ala Arg Arg
                1445                1450                1455
Phe Phe Leu Asp Ile Ala Ser Asp Cys Pro Thr Ser Asp Ala Val Asn
            1460                1465                1470
His Ser Leu Ser Phe Ile Ser Asp Gly Asn Val Leu Ala Leu His Arg
            1475                1480                1485
Leu Leu Trp Asn Asn Gln Glu Lys Ile Gly Gln Tyr Leu Ser Ser Asn
    1490                1495                1500
Arg Asp His Lys Ala Val Gly Arg Arg Pro Phe Asp Lys Met Ala Thr
1505                1510                1515                1520
Leu Leu Ala Tyr Leu Gly Pro Pro Glu His Lys Pro Val Ala Asp Thr
                1525                1530                1535
His Trp Ser Ser Leu Asn Leu Thr Ser Ser Lys Phe Glu Glu Phe Met
            1540                1545                1550
Thr Arg His Gln Val His Glu Lys Glu Glu Phe Lys Ala Leu Lys Thr
            1555                1560                1565
Leu Ser Ile Phe Tyr Gln Ala Gly Thr Ser Lys Ala Gly Asn Pro Ile
    1570                1575                1580
Phe Tyr Tyr Val Ala Arg Arg Phe Lys Thr Gly Gln Ile Asn Gly Asp
1585                1590                1595                1600
Leu Leu Ile Tyr His Val Leu Leu Thr Leu Lys Pro Tyr Tyr Ala Lys
                1605                1610                1615
Pro Tyr Glu Ile Val Val Asp Leu Thr His Thr Gly Pro Ser Asn Arg
            1620                1625                1630
Phe Lys Thr Asp Phe Leu Ser Lys Trp Phe Val Val Phe Pro Gly Phe
        1635                1640                1645
Ala Tyr Asp Asn Val Ser Ala Val Tyr Ile Tyr Asn Cys Asn Ser Trp
    1650                1655                1660
Val Arg Glu Tyr Thr Lys Tyr His Glu Arg Leu Leu Thr Gly Leu Lys
1665                1670                1675                1680
Gly Ser Lys Arg Leu Val Phe Ile Asp Cys Pro Gly Lys Leu Ala Glu
            1685                1690                1695
His Ile Glu His Glu Gln Gln Lys Leu Pro Ala Ala Thr Leu Ala Leu
                1700                1705                1710
Glu Glu Asp Leu Lys Val Phe His Asn Ala Leu Lys Leu Ala His Lys
    1715                1720                1725

```
Asp Thr Lys Val Ser Ile Lys Val Gly Ser Thr Ala Val Gln Val Thr
    1730            1735                1740

Ser Ala Glu Arg Thr Lys Val Leu Gly Gln Ser Val Phe Leu Asn Asp
1745            1750                1755                1760

Ile Tyr Tyr Ala Ser Glu Ile Glu Glu Ile Cys Leu Val Asp Glu Asn
                1765            1770                1775

Gln Phe Thr Leu Thr Ile Ala Asn Gln Gly Thr Pro Leu Thr Phe Met
            1780                1785            1790

His Gln Glu Cys Glu Ala Ile Val Gln Ser Ile Ile His Ile Arg Thr
        1795            1800            1805

Arg Trp Glu Leu Ser Gln Pro Asp Ser Ile Pro Gln His Thr Lys Ile
    1810            1815            1820

Arg Pro Lys Asp Val Pro Gly Thr Leu Leu Asn Ile Ala Leu Leu Asn
1825            1830            1835                1840

Leu Gly Ser Ser Asp Pro Ser Leu Arg Ser Ala Ala Tyr Asn Leu Leu
            1845            1850                1855

Cys Ala Leu Thr Cys Thr Phe Asn Leu Lys Ile Glu Gly Gln Leu Leu
            1860            1865            1870

Glu Thr Ser Gly Leu Cys Ile Pro Ala Asn Asn Thr Leu Phe Ile Val
        1875            1880            1885

Ser Ile Ser Lys Thr Leu Ala Ala Asn Glu Pro His Leu Thr Leu Glu
    1890            1895            1900

Phe Leu Glu Glu Cys Ile Ser Gly Phe Ser Lys Ser Ser Ile Glu Leu
1905            1910            1915                1920

Lys His Leu Cys Leu Glu Tyr Met Thr Pro Trp Leu Ser Asn Leu Val
            1925            1930            1935

Arg Phe Cys Lys His Asn Asp Asp Ala Lys Arg Gln Arg Val Thr Ala
            1940            1945            1950

Ile Leu Asp Lys Leu Ile Thr Met Thr Ile Asn Glu Lys Gln Met Tyr
            1955            1960            1965

Pro Ser Ile Gln Ala Lys Ile Trp Gly Ser Leu Gly Gln Ile Thr Asp
    1970            1975            1980

Leu Leu Asp Val Val Leu Asp Ser Phe Ile Lys Thr Ser Ala Thr Gly
1985            1990            1995                2000

Gly Leu Gly Ser Ile Lys Ala Glu Val Met Ala Asp Thr Ala Val Ala
            2005            2010            2015

Leu Ala Ser Gly Asn Val Lys Leu Val Ser Ser Lys Val Ile Gly Arg
            2020            2025            2030

Met Cys Lys Ile Ile Asp Lys Thr Cys Leu Ser Pro Thr Pro Thr Leu
        2035            2040            2045

Glu Gln His Leu Met Trp Asp Asp Ile Ala Ile Leu Ala Arg Tyr Met
    2050            2055            2060

Leu Met Leu Ser Phe Asn Asn Ser Leu Asp Val Ala Ala His Leu Pro
2065            2070            2075            2080

Tyr Leu Phe His Val Val Thr Phe Leu Val Ala Thr Gly Pro Leu Ser
            2085            2090            2095

Leu Arg Ala Ser Thr His Gly Leu Val Ile Asn Ile Ile His Ser Leu
            2100            2105            2110

Cys Thr Cys Ser Gln Leu His Phe Ser Glu Glu Thr Lys Gln Val Leu
            2115            2120            2125

Arg Leu Ser Leu Thr Glu Phe Ser Leu Pro Lys Phe Tyr Leu Leu Phe
    2130            2135            2140

Gly Ile Ser Lys Val Lys Ser Ala Ala Val Ile Ala Phe Arg Ser Ser
```

-continued

| 2145 | | | | 2150 | | | | 2155 | | | | 2160 | |

Tyr Arg Asp Arg Ser Phe Ser Pro Gly Ser Tyr Glu Arg Glu Thr Phe
                    2165                2170                2175

Ala Leu Thr Ser Leu Glu Thr Val Thr Glu Ala Leu Leu Glu Ile Met
                    2180                2185                2190

Glu Ala Cys Met Arg Asp Ile Pro Thr Cys Lys Trp Leu Asp Gln Trp
                    2195                2200                2205

Thr Glu Leu Ala Gln Arg Phe Ala Phe Gln Tyr Asn Pro Ser Leu Gln
                    2210                2215                2220

Pro Arg Ala Leu Val Val Phe Gly Cys Ile Ser Lys Arg Val Ser His
2225                2230                2235                2240

Gly Gln Ile Lys Gln Ile Ile Arg Ile Leu Ser Lys Ala Leu Glu Ser
                    2245                2250                2255

Cys Leu Lys Gly Pro Asp Thr Tyr Asn Ser Gln Val Leu Ile Glu Ala
                    2260                2265                2270

Thr Val Ile Ala Leu Thr Lys Leu Gln Pro Leu Leu Asn Lys Asp Ser
                    2275                2280                2285

Pro Leu His Lys Ala Leu Phe Trp Val Ala Val Ala Val Leu Gln Leu
                    2290                2295                2300

Asp Glu Val Asn Leu Tyr Ser Ala Gly Thr Ala Leu Leu Glu Gln Asn
2305                2310                2315                2320

Leu His Thr Leu Asp Ser Leu Arg Ile Phe Asn Asp Lys Ser Pro Glu
                    2325                2330                2335

Glu Val Phe Met Ala Ile Arg Asn Pro Leu Glu Trp His Cys Lys Gln
                    2340                2345                2350

Met Asp His Phe Val Gly Leu Asn Phe Asn Ser Asn Phe Asn Phe Ala
                    2355                2360                2365

Leu Val Gly His Leu Leu Lys Gly Tyr Arg His Pro Ser Pro Ala Ile
                    2370                2375                2380

Val Ala Arg Thr Val Arg Ile Leu His Thr Leu Leu Thr Leu Val Asn
2385                2390                2395                2400

Lys His Arg Asn Cys Asp Lys Phe Glu Val Asn Thr Gln Ser Val Ala
                    2405                2410                2415

Tyr Leu Ala Ala Leu Leu Thr Val Ser Glu Glu Val Arg Ser Arg Cys
                    2420                2425                2430

Ser Leu Lys His Arg Lys Ser Leu Leu Leu Thr Asp Ile Ser Met Glu
                    2435                2440                2445

Asn Val Pro Met Asp Thr Tyr Pro Ile His His Gly Asp Pro Ser Tyr
                    2450                2455                2460

Arg Thr Leu Lys Glu Thr Gln Pro Trp Ser Ser Pro Lys Gly Ser Glu
2465                2470                2475                2480

Gly Tyr Leu Ala Ala Thr Tyr Pro Thr Val Gly Gln Thr Ser Pro Arg
                    2485                2490                2495

Ala Arg Lys Ser Met Ser Leu Asp Met Gly Gln Pro Ser Gln Ala Asn
                    2500                2505                2510

Thr Lys Lys Leu Leu Gly Thr Arg Lys Ser Phe Asp His Leu Ile Ser
                    2515                2520                2525

Asp Thr Lys Ala Pro Lys Arg Gln Glu Met Glu Ser Gly Ile Thr Thr
                    2530                2535                2540

Pro Pro Lys Met Arg Arg Val Ala Glu Thr Asp Tyr Glu Met Glu Thr
2545                2550                2555                2560

Gln Arg Ile Ser Ser Ser Gln Gln His Pro His Leu Arg Lys Val Ser
                    2565                2570                2575

```
Val  Ser  Glu  Ser  Asn  Val  Leu  Leu  Asp  Glu  Glu  Val  Leu  Thr  Asp  Pro
               2580                    2585                    2590

Lys  Ile  Gln  Ala  Leu  Leu  Leu  Thr  Val  Leu  Ala  Thr  Leu  Val  Lys  Tyr
               2595                    2600                    2605

Thr  Thr  Asp  Glu  phe  Asp  Gln  Arg  Ile  Leu  Tyr  Glu  Tyr  Leu  Ala  Glu
          2610                    2615                    2620

Ala  Ser  Val  Val  Phe  Pro  Lys  Val  Phe  Pro  Val  Val  His  Asn  Leu  Leu
2625                     2630                     2635                     2640

Asp  Ser  Lys  Ile  Asn  Thr  Leu  Leu  Ser  Leu  Cys  Gln  Asp  Pro  Asn  Leu
               2645                    2650                    2655

Leu  Asn  Pro  Ile  His  Gly  Ile  Val  Gln  Ser  Val  Val  Tyr  His  Glu  Glu
               2660                    2665                    2670

Ser  Pro  Pro  Gln  Tyr  Gln  Thr  Ser  Tyr  Leu  Gln  Ser  Phe  Gly  Phe  Asn
               2675                    2680                    2685

Gly  Leu  Trp  Arg  Phe  Ala  Gly  Pro  Phe  Ser  Lys  Gln  Thr  Gln  Ile  Pro
          2690                    2695                    2700

Asp  Tyr  Ala  Glu  Leu  Ile  Val  Lys  Phe  leu  Asp  Ala  Leu  Ile  Asp  Thr
2705                     2710                     2715                     2720

Tyr  Leu  Pro  Gly  Ile  Asp  Glu  Glu  Thr  Ser  Glu  Glu  Ser  Leu  Leu  Thr
               2725                    2730                    2735

Pro  Thr  Ser  Pro  Tyr  Pro  Pro  Ala  Leu  Gln  Ser  Gln  Leu  Ser  Ile  Thr
               2740                    2745                    2750

Ala  Asn  Leu  Asn  Leu  Ser  Asn  Ser  Met  Thr  Ser  leu  Ala  Thr  Ser  Gln
               2755                    2760                    2765

His  Ser  Pro  Gly  Ile  Asp  Lys  Glu  Asn  Val  Glu  Leu  Ser  Pro  Thr  Thr
          2770                    2775                    2780

Gly  His  Cys  Asn  Ser  Gly  Arg  Thr  Arg  His  Gly  Ser  Ala  Ser  Gln  Val
2785                     2790                     2795                     2800

Gln  Lys  Gln  Arg  Ser  Ala  Gly  Ser  Phe  Lys  Arg  Asn  Ser  Ile  Lys  Lys
               2805                    2810                    2815

Ile  Val
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: Linear ( i i ) MOLECULE TYPE: protein ( i x ) FEATURE: Alternate splice version of NF1 in Marchuk, et al.,
           Genomics 11: 931-940 (1991), where the 21 amino acid
           sequence is inserted between amino acids 1370 and 1371.
           Please see Fig. 4.

( x i ) SEQUENCE DESCRIPTION: SEQ ID NO:2:

```
Ala  Thr  Cys  His  Ser  Leu  Ile  Asn  Lys  Ala  Thr  Val  Lys  Glu  Lys  Lys
1                   5                    10                       15

Glu  Asn  Lys  Lys  Ser
                20
```